United States Patent
van den Berg

(10) Patent No.: US 6,460,403 B1
(45) Date of Patent: Oct. 8, 2002

(54) DEVICE FOR ANALYSING PREFERABLY ANIMAL MANURE

(75) Inventor: Karel van den Berg, Bleskensgraaf (NL)

(73) Assignee: Lely Research Holding A.G., Zug (CH)

(*) Notice: Subject to any disclaimer, the term of this patent is extended or adjusted under 35 U.S.C. 154(b) by 0 days.

(21) Appl. No.: 09/765,387

(22) Filed: Jan. 22, 2001

Related U.S. Application Data

(63) Continuation of application No. PCT/NL00/00307, filed on May 10, 2000.

(30) Foreign Application Priority Data

May 25, 1999 (NL) .............................................. 1012136

(51) Int. Cl.$^7$ .......................... G01N 1/04; G01N 33/44; E03D 1/00; C02F 3/30; A61K 31/715
(52) U.S. Cl. .......................... 73/37; 73/54.12; 73/61.73; 73/54.02
(58) Field of Search ....................... 73/37, 54.11, 54.14, 73/54.03, 53.04, 61.73

(56) References Cited

U.S. PATENT DOCUMENTS

| | | | | |
|---|---|---|---|---|
| 4,170,798 A | * | 10/1979 | Krumdieck | .................... 4/319 |
| 5,252,460 A | * | 10/1993 | Fiedler et al. | .............. 435/7.22 |
| 5,355,833 A | | 10/1994 | Legrain | ................... 119/51.02 |
| 5,394,737 A | * | 3/1995 | Prange et al. | ................... 73/38 |
| 5,527,464 A | * | 6/1996 | Bartha et al. | ................ 210/603 |
| 5,616,569 A | * | 4/1997 | Reinhart | ....................... 514/54 |
| 5,998,695 A | * | 12/1999 | Roe et al. | .................... 604/367 |

FOREIGN PATENT DOCUMENTS

| | | | |
|---|---|---|---|
| DE | 3306476 | * | 8/1984 |
| GB | 2288879 A | | 11/1995 |
| NL | 9201359 | | 2/1994 |

* cited by examiner

*Primary Examiner*—Hezron Williams
*Assistant Examiner*—David J. Wiggins
(74) *Attorney, Agent, or Firm*—Penrose L. Albright

(57) ABSTRACT

A device which may be carried by and part of an unmanned vehicle which measures characteristics of manure of animals such as dairy cows that are milked and fed in a stable provided for them. The vehicle is supported by three driven wheels and carries a mechanism for analyzing manure which comprises a compression chamber for receiving a manure sample. A sieve is provided on one side of the chamber and a piston forces the manure sample through the sieve. By measuring the pressure required to squeeze the manure sample through the sieve, characteristics such as the fibrousness and the viscosity of the manure sample can be determined. The vehicle also carries an identification instrumentality for identifying the animal that provided the manure sample and may carry a temperature sensor and an inertia meter. It is operatively associated with a computer which registers data provided from analysis of each animal's manure sample and provides same as displayable data.

24 Claims, 1 Drawing Sheet

DEVICE FOR ANALYSING PREFERABLY ANIMAL MANURE

RELATED APPLICATION

This Application is a continuation of International Application No. PCT/NL00/00307, filed May 10, 2000.

FIELD OF THE INVENTION

The invention relates to a device for analyzing manure, preferably animal manure.

BACKGROUND OF THE INVENTION

Currently manure samples are analyzed on laboratory scales, usually very extensively. This is a complicated and very time-consuming activity.

SUMMARY OF THE INVENTION

An object of the invention is to provide a device of the above-mentioned type by means of which a diagnosis relating to the health and alimentary fitness of an animal can be made rather simply and quickly on the basis of an analysis of a manure sample.

In accordance with the invention this is achieved in that the device is provided with manure analyzing means for determining the composition or the viscosity or the fibrousness or any combination thereof of a manure sample. On the basis of the viscosity or the fibrousness or a combination thereof of the manure sample it is possible to determine whether the individual is receiving the correct amount of feed or whether the composition of the food is well attuned to the individual, or both.

According to an inventive feature, the manure analyzing means comprises a press with a compression chamber which is provided with at least one aperture via which the manure can flow out of the compression chamber during compression of the manure sample. In a preferred embodiment of the invention, the compression chamber comprises at least one wall which is designed as a sieve. According to the invention, the manure analyzing means further comprises force recording means with the aid of which a determination is made of the pressure or force which is required for compression of the manure sample. On the basis of the pressure or force so required during compression, the viscosity of the manure sample can subsequently be calculated. According to an inventive feature, for the purpose of establishing the percentage of fibers in the manure sample, the manure analyzing means comprises measuring means with the aid of which the amount of solid material is determined after compression. According to an inventive feature, the measuring means may comprise a clinometer. By means of the clinometer it is possible to establish to what extent the compression chamber has been reduced after compression, after which it is known how much remaining space of the compression chamber is filled with solid material.

In accordance with another inventive feature, the manure analyzing means comprises cleaning means with the aid of which the press can be cleaned after compression. This ensures that the press is not blocked or that the analysis of a new manure sample is not contaminated by analysis of the prior manure sample. According to an inventive feature, the manure analyzing means comprises a gripper. According to again another inventive feature, the manure analyzing means comprises a mass inertia meter. By shaking the manure sample it is possible to determine the mass inertia of the manure sample, said mass inertia being a measure for the viscosity of the manure sample. According to again another inventive feature, the manure analyzing means comprises a temperature sensor by means of which the temperature of the manure sample is determined. On the basis of the latter information it is possible to compensate influences of temperature on the viscosity of the manure.

According to a first embodiment of the invention, the manure analyzing means may be disposed in a toilet box. In a second embodiment of the invention, the manure analyzing means are arranged in a milking parlor or a feeding station or both. In a third embodiment of the invention, the manure analyzing means are disposed on an unmanned vehicle.

For the purpose of establishing which manure sample belongs to which individual, according to the invention the device comprises identification means with the aid of which the identity of the individual belonging to the manure sample is established. The identification means may be constituted by identification systems known per se, such as for example a cow recognition system.

According to again another inventive feature, the device comprises a computer which is adapted to convert the manure analysis results of the manure sample of a specific animal into a regimen of optimum food composition or feed distribution or both for such animal. Depending on the results of the manure analysis sample it is thus possible to alter the composition of the feed or to adjust the amount of feed or the point of time at which the feed is administered, or to perform any combination thereof for a specific animal. In an embodiment of the invention, the manure analysis results processed by the computer are supplied to a roughage or concentrate feeding station or both for controlling the distribution or the composition or both of the food which is supplied to the relevant animal.

BRIEF DESCRIPTION OF THE DRAWINGS

The invention will now be explained in further detail with reference to the accompanying drawings.

DETAILED DESCRIPTION OF THE PREFERRED EMBODIMENTS

Figure 1:
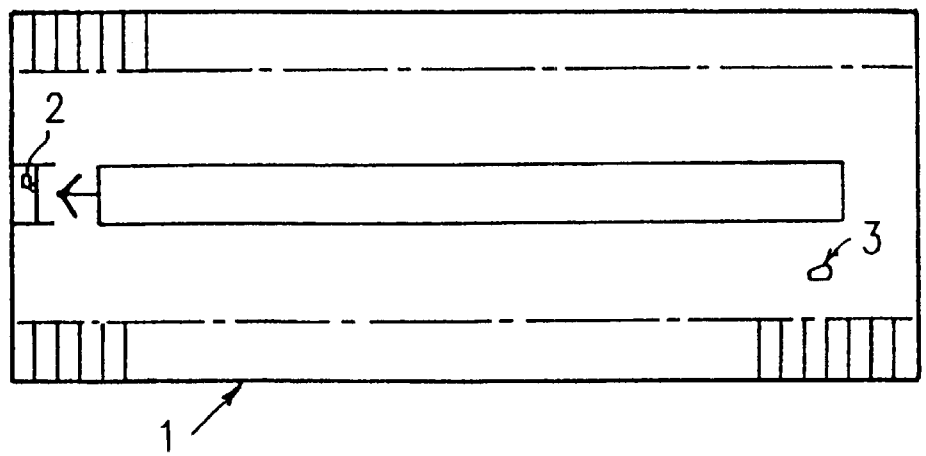
FIG. 1 is a plan view of a stable with an unmanned vehicle accommodated therein, on which vehicle the device according to the invention is disposed.

FIG. 1 is a plan view of a stable 1 provided with a milking robot 2 for automatically milking animals and an unmanned vehicle 3 on which a device 4 for analyzing a manure sample is disposed.

Figure 2:
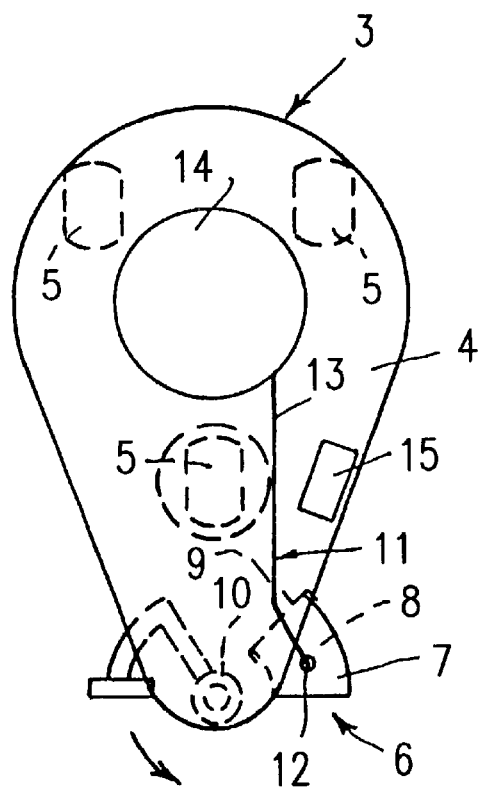
FIG. 2 is a plan view of the unmanned vehicle depicted in FIG. 1.

FIG. 2 is a plan view of the unmanned vehicle 3 which comprises wheels 5 that are driven by a drive unit. Unmanned vehicle 3 is further provided with manure analyzing means 6. In the present embodiment the manure analyzing means 6 comprise a gripper 7 including a chamber 8 for the manure sample, one wall 9 of gripper 7 being designed as a sieve. By means of a motor 10, wall 9 is rotated in the direction of chamber 8, which causes liquid components of the. manure to exit chamber 8 through the sieve in wall 9. A motor 10 is provided with a clinometer by means of which, after the manure sample has been compressed, the remaining contents of chamber 8 are determined. Chamber 8 then contains only solid components, such as fibers from the manure sample. Manure analyzing means 6 further comprises cleaning means 11 with the aid of which compression chamber 8 and wall 9 are cleaned. The cleaning means comprises a sprayer 12 which is connected to a liquid receptacle 14 by means of a pipe 13.

The manure analyzing means 6 is further provided with identification means 15 that the identifies the individual that provided to the relevant manure sample.

Figure 3:
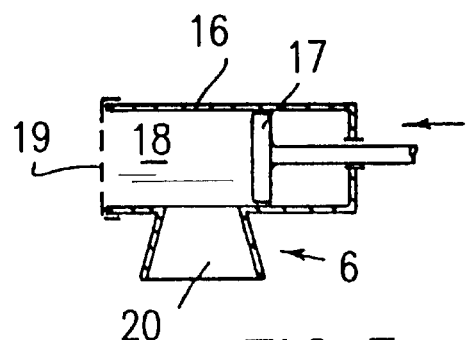
FIG. 3 is a longitudinal cross-section of a press with a compression chamber.

Instead of a gripper 7 it is further possible to provide manure analyzing means 6 in the form of a piston and cylinder arrangement. Such an embodiment is shown in FIG. 3. The manure analyzing means 6 in FIG. 3 comprises a cylindrical housing 16 with a piston 17 and a compression chamber 18. The end of compression chamber 18 is a sieve 19. Via the sieve 19 liquid components of the manure exit compression chamber 18 during compression. Compression chamber 18 is further connected to a filling member 20 by means of which the compression chamber 18 can be filled with a manure sample.

Figure 4:
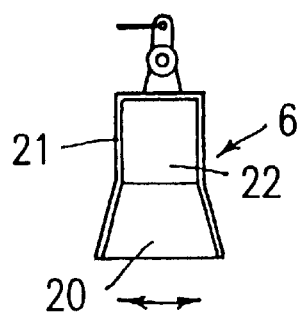
FIG. 4 depicts a manure analyzing means in the form of a mass inertia meter.

In FIG. 4 the manure analyzing means 6 comprise a mass inertia meter 21. Mass inertia meter 21 comprises a receptacle 22 into which a manure sample can be introduced, which receptacle 22 is pivoted by means of an operating member. During pivoting of receptacle 22 mass inertia of the manure sample is measured by means of a sensor. The mass inertia of the manure sample as so measured is converted by a computer into the viscosity of the manure sample.

Although I have disclosed the preferred embodiments of my invention, it is to be understood that it is capable of other adaptations and modifications within the scope of the following claims:

I claim:

1. A device for analyzing manure which comprises a chamber for receiving a manure sample, said chamber comprising at least one wall, an opening into said chamber for receiving said manure sample, pressure applying means for applying pressure against said manure sample while in said chamber, constricted outlet means comprising a sieve in said chamber through which manure exits from said chamber when said pressure applying means applies pressure against said sample, and manure analyzing means operatively associated with said chamber and said pressure applying means for determining at least one characteristic of said manure sample of a group characteristics consisting of said sample's composition, said sample's fibrousness, and said sample's viscosity.

2. A device for analyzing manure which comprises a chamber for receiving a manure sample, an opening in said chamber for receiving said manure sample, pressure applying means for applying pressure against said manure sample while in said chamber, constricted outlet means in said chamber through which said manure exits from said chamber when said pressure applying means applies pressure against said sample, and manure analyzing means operatively associated with said chamber and said pressure applying means for determining at least one characteristic of said manure sample of a group of characteristics consisting of said sample's composition, said sample's fibrousness, and said sample's viscosity, said manure analyzing means comprising measuring means for determining the amount of solid material after said manure sample has been compressed by said pressure applying means in said chamber, said measuring means comprising a clinometer.

3. A device for analyzing manure which comprises a chamber for receiving a manure sample, an opening into said chamber for receiving said manure sample, pressure applying means for applying pressure against said manure sample while in said chamber, constrictive outlet means in said chamber through which manure exits from said chamber when said pressure applying means applies pressure against said sample, and manure analyzing means operatively associated with said chamber and said pressure applying means for determining at least one characteristic of said manure sample of a group of characteristics consisting of said sample's composition, said sample's fibrousness, and said sample's viscosity, said manure analyzing means comprising a mass inertia meter.

4. A device for analyzing manure which comprises a chamber for receiving a manure sample, an opening into said chamber for receiving said manure sample, pressure applying means for applying pressure against said manure sample while in said chamber, constricted outlet means in said chamber through which said manure exits from said chamber when said pressure applying means applies pressure against said sample, manure analyzing means operatively associated with said chamber and said pressure applying means for determining at least one characteristic of said manure sample of a group of characteristics consisting of said sample's composition, said sample's fibrousness and said sample's viscosity, and a computer which receives data from said manure analyzing means and from an animal identification means that identifies the animal that provided said manure sample, said data being registered for said identified animal in said computer, said data further being registered so that said data are visually displayable, said visually displayable data including data as to the force applied by said pressure applying means against said sample.

5. A device for analyzing manure which comprises a chamber for receiving a manure sample, an opening into said chamber for receiving said manure sample, pressure applying means for applying pressure against said manure sample while in said chamber, constricted outlet means in said chamber through which manure exits from said chamber when said pressure applying means applies pressure against said sample, manure analyzing means operatively associated with said chamber and said pressure applying means for determining at least one characteristic of said manure sample of a group of characteristics consisting of said sample's composition, said sample's fibrousness and said sample's viscosity, a computer that receives data from said manure analyzing means, adjustable threshold values of said data inputed into said computer, and separation means for placing an animal in a separation area which is controlled by said computer and when at least of one said threshold value is exceeded said separation means causes the animal providing said manure sample to be placed in said separation ares.

6. A device for analyzing a manure sample comprising a compression chamber for receiving a manure sample, an identification means for identifying an animal providing said manure sample, said chamber having an opening for receiving said manure sample, pressure applying means for applying pressure against said manure sample while in said chamber, a constricted outlet means in said chamber through which said manure sample is squeezed from said chamber when said pressure applying means applies pressure against said sample, a computer operably associated with said chamber and said pressure applying means for recording the pressure require by said pressure applying means to squeeze said manure sample from said chamber and registering said pressure for said animal identified by said identification means.

7. A device for analyzing manure of farm animals which comprises a chamber for receiving a manure sample from one of said farm animals, an opening into said chamber for receiving said manure sample, pressure applying means in said chamber for applying pressure against said manure sample while in said chamber, a constricted outlet means in said chamber through which said manure exits from said chamber as result of the pressure applied against said manure sample by said pressure applying means, and manure analyzing means operatively associated with said chamber and said pressure applying means for determining at least one characteristic of said manure sample of a group of characteristics consisting of sample's composition, said sample's fibrousness, and said sample's viscosity.

8. A device in accordance with claim 7 wherein said constriction outlet means comprises at least one aperture via which manure from said manure sample flows out of said chamber during compression of said manure sample in said chamber.

9. A device in accordance with claim 7 wherein said manure analyzing means comprises force recording means for determining the pressure applied against said manure sample by said pressure applying means.

10. A device in accordance with claim 7 wherein said manure analyzing means comprises measuring means for determining the amount of solid material after said manure sample has been compressed by said pressure applying means in said chamber.

11. A device in accordance with claim 7 wherein said manure analyzing means comprises cleaning means for cleaning said chamber.

12. A device in accordance with claim 7 wherein said manure analyzing means comprises a temperature sensor that measures the temperature of said manure sample.

13. A device in accordance with claim 7 wherein said manure analyzing means is disposed in a toilet box.

14. A device in accordance with claim 7 wherein said manure analyzing means is arranged in a milking compartment.

15. A device in accordance with claim 7 wherein said manure analyzing means is arranged at a feeding station.

16. A device in accordance with claim 7 wherein said manure analyzing means is carried by an unmanned vehicle.

17. A device in accordance with claim 7 which further comprises identification means for identifying the individual animal that provides said manure sample.

18. A device in accordance with claim 7 which comprises a computer which is programmed to determine on the basis of the manure analysis results of said manure sample from a specific animal an optimum composition of food to be fed to said specific animal.

19. A device in accordance with claim 7 which further comprises a computer that is programmed to determine on the basis of the manure analysis results of said manure sample of a specific animal, an optimum amount of feed to be distributed to said specific animal.

20. A device in accordance with claim 7 which comprises a computer which is programmed to determine on the basis of the manure analysis results of said manure sample of a specific animal, the optimum amount of roughage and concentrates to be distributed to said specific animal, said manure analysis results from said computer being supplied to a mixing and distribution means for preparing food to be distributed to said specific animal.

21. A device in accordance with claim 7 comprising a computer which receives data from said manure analyzing means and from an animal identification means that identifies the specific animal that provided said manure sample, said data being registered for said identified animal in a computer.

22. A device in accordance with claim 21 wherein said data are registered so that said data are visually displayable.

23. A device in accordance with claim 7 which comprises a computer into which one or more adjustable threshold values which are provided by said manure analyzing means have been inputed and signalling means for alerting an operator of the device of the identity of an animal that provided said manure sample that exceeded threshold value.

24. A device in accordance with claim 7 wherein said chamber comprises a gripper.

* * * * *